United States Patent [19]

Mellul et al.

[11] Patent Number: 5,578,297
[45] Date of Patent: Nov. 26, 1996

[54] COSMETIC COMPOSITIONS CONTAINING AN EXPOXIDIZED OIL AS PLASTICIZER

[75] Inventors: Myriam Mellul, L'Hay Les Roses; Valérie de la Poterie, Le Chatelet en Brie, both of France

[73] Assignee: L'Oreal, France

[21] Appl. No.: 313,784

[22] Filed: Sep. 28, 1994

[30] Foreign Application Priority Data

Sep. 28, 1993 [FR] France .................................. 93 11501

[51] Int. Cl.⁶ .......................... A61K 7/032; A61K 7/043; A61K 7/06
[52] U.S. Cl. ...................... 424/70.7; 424/61; 424/70.11; 424/70.13; 424/401
[58] Field of Search ............................. 424/61, 401, 70.7, 424/70.11, 70.13

[56] References Cited

U.S. PATENT DOCUMENTS 3,953,650  4/1976  Sauer et al. ............................. 428/389

FOREIGN PATENT DOCUMENTS 2591104  6/1987  France .
2679445  1/1993  France .

OTHER PUBLICATIONS

Derwent Abstract of French Pat. Appl. FR 2,591,104, Jun. 12, 1987.
Derwent Abstract of French Pat. Appl. FR 2,679,445, Jan. 29, 1993.
Chemical Abstract 120(16):194059r.

Primary Examiner—Jyothsna Venkat
Attorney, Agent, or Firm—Finnegan, Henderson, Farabow, Garrett & Dunner

[57] ABSTRACT

The invention relates to a cosmetic composition, for example, a nail varnish, comprising a film-forming material, at least one plasticizer comprising an epoxidized oil such as Vernonia oil and at least one solvent.

13 Claims, No Drawings

COSMETIC COMPOSITIONS CONTAINING AN EXPOXIDIZED OIL AS PLASTICIZER

The present invention relates to a film-forming cosmetic composition, for example, nail varnish, colourless or coloured, containing, beside the usual constituents, an epoxidized oil as a plasticizer.

Main characteristics of film-forming cosmetic compositions such as nail varnishes, include, for example, the absence of irritation of the support, i.e., skin, nails and/or hair; good application; the obtaining of a homogeneous film having excellent gloss; a rapid drying time of the film, but also good adhesion to the surface of the support; and some degree of flexibility and good strength of the film, for example, so as to avoid cracks and chipping of the film. These characteristics are generally designated cosmetic characteristics.

Generally speaking, film-forming materials such as nitrocellulose, combined, if necessary, with another polymer such as a toluenesulphonamide-formaldehyde resin or an alkyd resin and plasticizers, are used at the present time, for example, in nail varnishes, to confer good adhesion and good flexibility of the film (see, in this connection, in particular, the document FR-A-2,679,445, the disclosure of which is specifically incorporated by reference herein). The plasticizers commonly used are plasticizers of the phthalate type such as dibutyl phthalate; of the citrate type such as tributyl acetylcitrate; of the glycol ester type such as neopentyl glycol ester or propylene glycol ester; of the glyceryl benzoate type; and lastly, camphor. These plasticizing agents enable the flexibility of the film to be adjusted without weakening its physical strength.

Nowadays, it is preferable to use plasticizers other than phthalates in varnishes for reasons of allergy, but also other than camphor which, owing to its volatility, makes it difficult to achieve constant varnish characteristics. Moreover, it is preferable, and also for reasons of allergy, to avoid the use of a polymer which is a source of formaldehyde.

For the purpose of applying varnish to the nails, liquid compositions containing a large amount of organic solvent (in general approximately 70% by weight of the total composition) are used at the present time. Now, for reasons of pollution of the environment, it is sought to decrease the solvent amount.

Moreover, the formulation of nail varnishes is exacting, since the composition involves judicious matching between the different constituents. Thus, the change in one of these constituents can considerably modify the cosmetic properties of the varnish, such as application, gloss, drying, hardness or hold of the film, making this varnish unsuitable for use. For these reasons, the nail varnish formulations currently available on the market are virtually identical or even identical.

The invention provides a new cosmetic composition which makes it possible, in particular, to remedy the above drawbacks but still provide excellent cosmetic properties.

The invention can also reduce or even eliminate the common plasticizers used in the prior art, and also reduce the amount of solvent.

The invention can also provide new hypoallergenic compositions.

Surprisingly, it was found that an epoxidized oil could be used as a plasticizer in cosmetic compositions containing an organic medium, without modifying the cosmetic properties of the film formed. This oil may be used alone or, where appropriate, combined with another plasticizer known to a person skilled in the art.

More specifically, the invention relates to a cosmetic composition comprising at least one solvent, at least one film-forming material, an effective amount of at least one plasticizer, wherein the plasticizer comprises at least one epoxidized oil, and wherein at least one of the film forming materials and at least one of the plasticizers are different. This oil can be synthetic or, advantageously, natural.

As natural oils, vegetable oils such as epoxidized soyabean oil, epoxidized linseed oil and, preferably, epoxidized Vernonia oil, as well as mixtures thereof, may be mentioned. A preferred viscosity for such suitable epoxidized oils, particularly when the cosmetic composition of the invention is intended for use as a nail varnish composition, is in the range from 200 to 400 mPa.s.

Vernonia oil, and more exactly that of *Vernonia galamensis*, is of the triglyceride type whose general fatty acid composition is as follows:

| | | |
|---|---|---|
| vernolic acid | C 18:1 (unsaturated) | 72.0–80.0% |
| palmitic acid | C 16:0 | 2.0–3.0% |
| stearic acid | C 18:0 | 2.0–4.0% |
| oleic acid | C 18:1 | 4.0–6.0% |
| linoleic acid | C 18:2 | 11.0–14.0% |

The Vernonia oil used in the present invention is a refined vegetable oil obtained by cold pressing of deactivated crushed Vernonia seeds. This refined oil is a transparent yellow homogeneous liquid which is completely soluble in most organic solvents. The advantage of this oil is its low viscosity (of the order of 300 mPa.s), which enables it to be introduced in greater or lesser amounts without significantly modifying, relative to the traditional compositions, the viscosity of the medium. This low viscosity makes it possible, in addition, to decrease, relative to the known compositions, the amount of solvent. To date, the only known use of Vernonia oil is as a diluent in paints (see, in this connection, the article by S. Dirlikov et al., "Increasing high-solids with a weed", Agro-industrial Finishing, p. 17–19).

The composition of the invention preferably contains, by weight, from 0.5% to 25% of plasticizer, from 5% to 35% of film-forming material other than the plasticizer and 40% to 90% of solvent, or in other words, solvent medium. More preferably, the composition of the invention contains from 3 to 15% of plasticizer, from 15% to 35% of film-forming material other than the plasticizer and from 50% to 82% of solvent. With these compositions, it is possible to obtain dry extracts, i.e., the percentage of the weight of the solid matter, such as film-forming component and plasticizer in the cosmetic composition relative to the total weight of the composition, ranging from 20% to 50% by weight. Preferably, dry extracts are obtained which range from 20 to 40% by weight, more preferably from 25% to 40%, and most preferably from 20 to 35%.

In addition, the epoxidized oil can be present at percentages greater than 9% by weight of the total composition in varnishes having a high dry extract without significantly modifying the viscosity, thus giving varnishes having a reduced content of volatile products and possessing excellent cosmetic characteristics.

Adjunct plasticizers which are usable in combination with the epoxidized oil are, for example, those mentioned in the document FR-A-2,679,445, such as dibutyl, dioctyl, diisobutyl and dimethoxyethyl phthalates; benzyl and glyceryl benzoates; triethyl and tributyl citrates, tributyl acetylcitrate; tributyl and triphenyl phosphates; glycols; and camphor, as well as their derivatives and mixtures thereof. These adjunct plasticizers represent at most 50% by weight of the total amount of plasticizer.

The film-forming materials of the invention comprise especially nitrocellulose, optionally combined with an alkyd, polyurethane, acrylic, vinyl, arylsulphonamide-formaldehyde or arylsulphonamide-epoxy resin, and, generally speaking, any resin compatible with the medium. These resins enable the film-forming power of nitrocellulose to be increased and improve the gloss as well as the adhesion of the films.

The resin preferably combined with nitrocellulose is the toluenesulphonamide-urea-formaldehyde resin better known under the trade names "Santolite MHP", "Santolite MS 80%" and "Ketjenflex MS80". This resin possesses excellent film-forming properties. More preferably, the resin used is an alkyd resin, for example, of the glycerophthalic alkyd type (BECKOSOL ODE). Alkyd resins have the advantages of not containing formaldehyde and of being hypoallergenic.

Thus, preferably, the composition of the invention contains mainly nitrocellulose, an alkyd resin, Vernonia oil and at least one solvent. This composition possesses excellent cosmetic characteristics. It is, in addition, possible to replace nitrocellulose by a polyvinyl resin such as polyvinyl butyrate.

According to the invention, the solvent is preferably a mixture of solvents, and particularly a mixture of various volatile organic solvents, the purpose of using volatile solvents being to obtain relatively short drying times. The solvents used must be compatible with the resins used in order to effect their dissolution.

preferred solvents are those traditionally used in cosmetic compositions. Among these solvents, there may be mentioned ketones such as acetone, methyl ethyl ketone, methyl isobutyl ketone; glycol ethers; alcohols such as ethanol, n-butanol, n-propanol, isopropanol; acetates such as butyl, ethyl and isopropyl acetate, 2-methoxyethyl acetate; linear or branched hydrocarbons such as hexane or octane; or alternatively, aromatic hydrocarbons such as xylene and toluene. Preferably, butyl and ethyl acetates are used.

When the cosmetic composition takes the form of a coloured nail varnish, at least one pigment of an organic or inorganic nature is then used. Among organic pigments, there may be mentioned D & C Red nos. 10, 11, 12 and 13, D & C Red no. 7, D & C Red nos. 5 and 6, D & C Red no. 34, and lakes such as D & C Yellow no. 5 lake and D & C Red no. 2 lake. Guanine may also be mentioned as an organic pigment.

Among inorganic pigments, titanium dioxide, bismuth oxychloride, brown iron oxide and red iron oxides may be mentioned.

According to this embodiment, the pigments are generally present in a proportion ranging from 0.01% to 2.5% by weight relative to the total weight of the varnish.

Moreover, in order to avoid sedimentation of the pigments, some thixotropic rheological agents may be employed, such as clays of the "Bentone 27", "Bentone 38" or montmorillonite type. These agents serve, in addition, as thickeners. Preferably, these agents are acidified using citric acid.

The nail varnishes according to the invention can, moreover, contain adjuvants commonly used in nail varnishes. Among these adjuvants, there may be mentioned UV screening agents such as benzophenone derivatives and ethyl 2 cyano-3,3-diphenylacrylate, colorants and also silicones and fluorinated agents. Preferably, these adjuvants are used at a concentration at most equal to 1% by weight relative to the total weight of the varnish.

The compositions according to the invention can be mainly used as nail varnishes. It is also possible to envisage using them as a make-up product, for example, mascara, or a hair-care product. In this case, the compositions can contain, in addition, the constituents commonly used in these applications, which constituents are well known to a person skilled in the art.

Several examples of nail varnish compositions according to the invention will now be given by way of illustration and without any implied limitation, together with comparative examples.

All the compositions below were obtained at room temperature, by solubilizing nitrocellulose in the solvent (acetate), adding the epoxidized oil and then the alkyd or formaldehyde resin, and then dispersing the solid additives such as the clay type rheological agents as well as citric acid and the pigments.

The nitrocellulose is used dissolved in isopropanol at a concentration of 70% by weight. The alkyd resin (BECKOSOL ODE) and the formaldehyde resin (Santolite Ketjenlex MS80) are dissolved, respectively, at a concentration of 70% by weight in xylene and 80% by weight in butyl acetate.

The compositions are presented in the form of Tables I and II and, for each composition, the amount of corresponding dry extract, their drying time and their viscosity are shown, together with the hardness, gloss and surface energy of the films obtained. Tables I and II relate, respectively, to colourless nail varnishes and nail varnishes coloured red with D & C Red no. 7 pigment. D & C Red no. 7 was used in a dispersion in the control colourless base (sample A) at 4% by weight.

Hardness is determined at the surface by measuring the time of swing of a pendulum in contact with the film; it should be between 20 s and 150 s, and preferably between 30 s and 80 s, in order to be satisfactory. It is measured in a chamber thermostated at 30° C. with a constant 70% degree of humidity (RH).

Gloss corresponds to the coefficient of luminous reflection of the film; it should be greater than 75%, and preferably in the region of 90%.

The surface energy characterizes the surface of the film, and in particular its capacity for wetting of the support.

Drying time is measured in an atmosphere controlled with respect to temperature (30° C.) and to humidity (50% RH), using a circular-motion ball apparatus (Braive Instruments Model No. 55-50), wherein a ball, travelling in a circular motion, passes over the film of varnish 300 µm thick spread on a glass plate. It should be noted that the time measured according to this technique is reproducible but greater than the drying time on a nail.

In Table I, it is seen that the characteristics of the films obtained from the compositions B, D and G of the invention are comparable to those obtained from the control compositions A, which contain Citroflex as plasticizer. Compositions C, E, and H are comparative compositions.

The composition C results in an excessively hard dry extract, since the amount of Vernonia oil is insufficient.

The composition E shows a fall in gloss and an increase in hardness relative to the compositions B and D, showing that Vernonia oil is better than linseed oil. It should be noted, however, that the linseed oil used here was non-epoxidized.

The composition H, for a higher dry extract than that of the compositions A to G, indicates an insufficiency of the Vernonia oil as a result of the viscosity and the great hardness. By increasing the amount of oil to more than 9% by weight of the composition, there is obtained, with a comparable dry extract, a composition I of the invention for which the viscosity goes down and the hardness of the film decreases. On comparing the composition I with the control composition J, it is seen that their viscosity and their surface energy are comparable. On the other hand, the composition I of the invention is glossier than that of composition J.

Thus, Vernonia oil is a good plasticizer of varnishes having a high dry extract.

In Table II, the samples Ac, Bc, Cc and Dc correspond to the samples A, B, C and D to which the pigment D & C Red no. 7 has been added. From this Table II, it is seen that the addition of a pigment to the compositions B, C and D causes little or no modification of the properties of the nail varnish. The gloss, though slightly lower than that of the colourless compositions on account of the pigment, is entirely acceptable. In addition, these coloured compositions do not display, 6 months after manufacture, any sedimentation of the pigment, and display good stability.

2. The composition according to claim 1, wherein the epoxidized oil is Vernonia oil, soya-bean oil, or linseed oil.

3. The composition according to claim 2, wherein the epoxidized oil is Vernonia oil.

4. The composition according to claim 1, comprising, by weight, from 3% to 15% of a plasticizer, from 5% to 35% of film-forming material comprising nitrocellulose, and from 50% to 82% of a solvent or mixture of solvents.

5. The composition according to claim 1, wherein the film-forming material comprises, in addition, at least one arylsulphonamide-formaldehyde resin, at least one alkyd resin, or a mixture of at least one arylsulphonamide-formaldehyde resin and at least one alkyd resin.

6. The composition according to claim 1, comprising nitrocellulose, an alkyd resin, Vernonia oil and a solvent medium.

TABLE I

| COLOURLESS SAMPLES | A (CONTROL) | B | C (COMP.) | D | E (COMP.) | F (CONTROL) | G | H (COMP.) | I | J (CONTROL) |
|---|---|---|---|---|---|---|---|---|---|---|
| Nitrocellulose (70%) | 14 | 14 | 16.66 | 14 | 14 | 14 | 14 | 18.83 | 17.5 | 17.5 |
| ODE (70%) | 15 | 15 | 17.84 | 15 | 15 | — | — | 20.17 | 18.75 | 18.75 |
| Santolite (80%) | — | — | — | — | — | 13.125 | 13.125 | — | — | — |
| Citroflex | 7.7 | 3.85 | — | — | — | 7.7 | — | — | — | 9.625 |
| Vernonia oil | — | 3.85 | 3.85 | 7.7 | — | — | 7.7 | 7.7 | 9.625 | — |
| Linseed Oil | — | — | — | — | 7.7 | — | — | — | — | — |
| Butyl acetate | 36.78 | 36.78 | 35.79 | 36.78 | 36.78 | 37.905 | 37.905 | 30.78 | 31.275 | 31.275 |
| Ethyl acetate | 24.52 | 24.52 | 23.86 | 24.52 | 24.52 | 25.27 | 25.27 | 20.52 | 20.85 | 20.85 |
| Citric acid | 0.5 | 0.5 | 0.5 | 0.5 | 0.5 | 0.5 | 0.5 | 0.5 | 0.5 | 0.5 |
| Bentone 27 | 1.5 | 1.5 | 1.5 | 1.5 | 1.5 | 1.5 | 1.5 | 1.5 | 1.5 | 1.5 |
| Dry Extract | 28% | 28% | 28% | 28% | 28% | 28% | 28% | 35% | 35% | 35% |
| Nitro/resin ratio | 0.93 | 0.93 | 0.93 | 0.93 | 0.93 | 0.93 | 0.93 | 0.93 | 0.93 | 0.93 |
| Viscosity mPa · s | 253 | 261 | 406 | 299 | 287 | 222 | 220 | 1038 | 693 | 675 |
| Hardness | 30.4 | 48.0 | 163.3 | 50.4 | 137.9 | 21.9 | 49.6 | 78.1 | 50.9 | 31.0 |
| Gloss | 88.00 | 87.6 | 87.7 | 86.2 | 81.9 | 91.3 | 95.7 | 87.8 | 90.4 | 85.2 |
| Surface energy | 40.1 | 39.8 | 37.8 | 40.8 | 38.7 | 40.9 | 42.2 | 39.7 | 39.6 | 39.3 |
| Drying (min) | 15 | 15 | 12.5 | | | | | | | |

TABLE II

| COLOURED SAMPLES | Ac (Control) | Bc | Cc (COMPARATIVE) | Dc |
|---|---|---|---|---|
| Nitrocellulose (70%) | 12.6 | 12.6 | 14.994 | 12.6 |
| ODE (70%) | 13.5 | 13.5 | 16.056 | 13.5 |
| Citroflex | 6.93 | 3.465 | — | — |
| Vernonia oil | — | 3.465 | 3.465 | 6.93 |
| Butyl acetate | 33.102 | 33.102 | 32.211 | 33.102 |
| Ethyl acetate | 22.068 | 22.068 | 21.474 | 22.068 |
| Citric acid | 0.45 | 0.45 | 0.45 | 0.45 |
| Bentone 27 | 1.35 | 1.35 | 1.35 | 1.35 |
| D & C Red no. 7 pigment | 10 | 10 | 10 | 10 |
| Dry Extract | 28% | 28% | 28% | 28% |
| Nitro/resin ratio | 0.93 | 0.93 | 0.93 | 0.93 |
| Hardness | 32.8 | 45.7 | 156.6 | 62.0 |
| Gloss | 84.7 | 84.8 | 84.7 | 84.0 |
| Surface energy | 40.6 | 39.4 | 39.1 | 39.9 |

We claim:

1. A composition comprising from:
   (a) 0.5 to 25% of a plasticizer comprising an epoxidized oil,
   (b) 5 to 35% of a film-forming material comprising nitrocellulose, and
   (c) 40–90% of a solvent or mixture of solvents.

7. The composition according to claim 1, wherein the composition further comprises at least one pigment.

8. The composition according to claim 7, wherein said at least one pigment is present at a concentration of 0.01% to 2.5% by weight relative to the total weight of the composition.

9. The composition according to claim 1, wherein the composition is a nail varnish composition.

10. The composition according to claim 1, wherein the solvent or solvents in the mixture comprise butyl acetate and ethyl acetate.

11. A method of coating a human nail comprising applying to the nail a film of an effective amount of a cosmetic composition comprising an effective amount of at least one plasticizer, at least one film-forming material other than said plasticizer and a solvent, wherein the plasticizer comprises at least one epoxidized oil.

12. A method of applying mascara to a human eyelash comprising the step of applying to the eyelash a mascara product containing an effective amount of a cosmetic composition comprising an effective amount of at least one plasticizer, at least one film-forming material other than said plasticizer and a solvent, wherein the plasticizer comprises at least one epoxidized oil.

13. A method of treating human hair comprising the step of applying to the hair a hair-care product containing an effective amount of a cosmetic composition comprising an effective amount of at least one plasticizer, at least one film-forming material other than said plasticizer and a solvent, wherein the plasticizer comprises at least one epoxidized oil.

* * * * *